(12) United States Patent
Roman et al.

(10) Patent No.: US 9,274,062 B2
(45) Date of Patent: Mar. 1, 2016

(54) OPTICAL METHOD FOR INSPECTING TRANSPARENT OR TRANSLUCENT CONTAINERS BEARING VISUAL

(71) Applicant: MSC & SGCC, Vourles (FR)

(72) Inventors: Sebastien Roman, La Fouillouse (FR); Nicolas Ploton, Lyons (FR)

(73) Assignee: MSC & SGCC, Vourles (FR)

( * ) Notice: Subject to any disclaimer, the term of this patent is extended or adjusted under 35 U.S.C. 154(b) by 0 days.

(21) Appl. No.: 14/402,747

(22) PCT Filed: May 28, 2013

(86) PCT No.: PCT/FR2013/051178
§ 371 (c)(1),
(2) Date: Nov. 21, 2014

(87) PCT Pub. No.: WO2013/178928
PCT Pub. Date: Dec. 5, 2013

(65) Prior Publication Data
US 2015/0146965 A1    May 28, 2015

(30) Foreign Application Priority Data

May 28, 2012    (FR) ..................... 12 54903

(51) Int. Cl.
*G06K 9/00*  (2006.01)
*G01N 21/90*  (2006.01)
(Continued)

(52) U.S. Cl.
CPC ............ *G01N 21/90* (2013.01); *G01N 21/8806* (2013.01); *G01N 21/9036* (2013.01); *G01N 21/9045* (2013.01); *G01N 21/93* (2013.01); *G01N 21/958* (2013.01); *G06T 7/0042* (2013.01); *G01N 2201/12* (2013.01);
(Continued)

(58) Field of Classification Search
CPC .. G01N 21/90; G01N 21/8806; G06T 7/0042; G06T 2207/10004
USPC ......................................................... 382/141
See application file for complete search history.

(56) References Cited

U.S. PATENT DOCUMENTS

| | | | | |
|---|---|---|---|---|
| 5,095,204 | A * | 3/1992 | Novini | G01N 21/9045 250/223 B |
| 6,025,910 | A | 2/2000 | Lucas | |
| 2005/0259868 | A1 | 11/2005 | Sones | |
| 2013/0271755 | A1* | 10/2013 | Lindner | G01N 21/90 356/240.1 |
| 2015/0071523 | A1* | 3/2015 | Herrmann | G01N 21/90 382/142 |

FOREIGN PATENT DOCUMENTS

| | | |
|---|---|---|
| EP | 1 560 018 | 8/2005 |
| EP | 1 916 515 | 4/2008 |

(Continued)

*Primary Examiner* — Ruiping Li
(74) *Attorney, Agent, or Firm* — Clark & Brody

(57) ABSTRACT

An optical method of inspecting containers comprises taking an image of each container and determining a search zone in each image of the container, a visible pattern appearing in the search zone. A digital mask is prepared for a treatment zone of the images including the visible pattern and at least each pixel of the treatment zone of the images is compared with a digital mask. A visible pattern is selected belonging to the container and the position and the orientation of the selected visible pattern in said search zone is determined. A geometrical transformation is applied to the digital mask or to the treatment zone to place the mask and the treatment zone in a position in which they coincide. Image treatment is applied to each pixel of the treatment zone, which treatment depends on the intensity value of the coincident pixel of the digital mask.

7 Claims, 2 Drawing Sheets

(51) Int. Cl.
*G01N 21/93* (2006.01)
*G01N 21/88* (2006.01)
*G01N 21/958* (2006.01)
*G06T 7/00* (2006.01)

(52) U.S. Cl.
CPC ............... *G06T2207/10004* (2013.01); *G06T 2207/30204* (2013.01)

(56) References Cited

FOREIGN PATENT DOCUMENTS

| | | |
|---|---|---|
| FR | 2 916 048 | 11/2008 |
| FR | 2 939 201 | 6/2010 |
| WO | 97/06429 | 2/1997 |

* cited by examiner

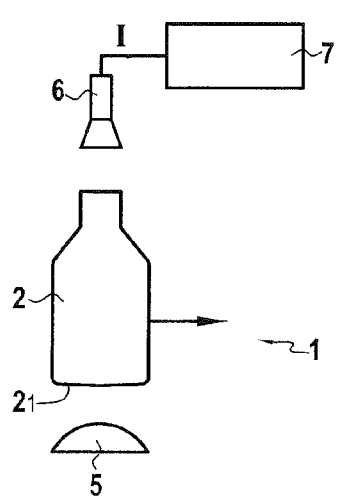
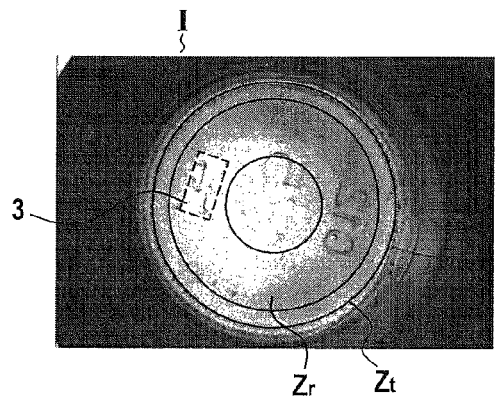
FIG.1    FIG.1A
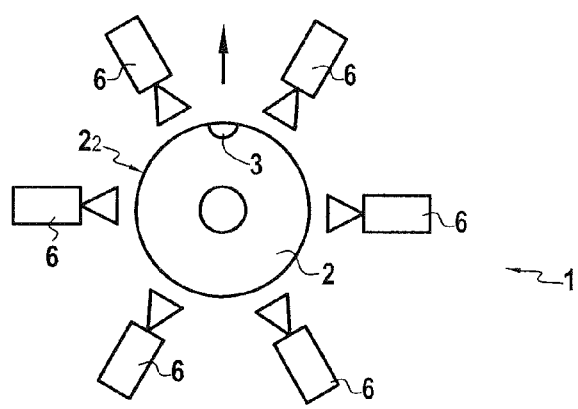
FIG.2

OPTICAL METHOD FOR INSPECTING TRANSPARENT OR TRANSLUCENT CONTAINERS BEARING VISUAL

The present invention relates to the technical field of optically inspecting translucent or transparent containers in order to detect light absorbing and/or refracting and/or reflecting defects, if any, presented by such containers.

The invention finds a particularly advantageous application in detecting defects in containers made of glass or plastics material and that include visible patterns in the broad sense, such as decoration, crests, positioning lugs or notches, and/or identification or authentication marks such as mold numbers or a trademark of the manufacturer, etc.

On a production line, it is known to perform automatic inspection on containers traveling at a high rate past an optical inspection station that includes a vision system having a light situated on one side of the container and a camera situated on the other side of the container. The camera takes images as a result of light passing through the containers. This lighting technique is said to be by "transmission". Naturally, a plurality of inspection stations are needed in order to inspect the containers in full. Thus, it is known to use equipment comprising six to twenty-four cameras for inspecting the vertical walls of containers. In order to inspect the bottoms of the containers, another vision system is provided in which the camera is situated above the container and the light source beneath the bottom of the container. An image of the bottom of the container is taken through its neck. Other optical systems are used, with light that may optionally be structured, optionally collimated, optionally polarized, etc.

Additional other devices may be used for detecting defects that reflect light, such as for example glaze.

Those optical devices all have in common a step of obtaining at least one image of each container for inspection.

In general terms, the images of the containers are analyzed by electronic treatment systems that consist in digitizing the images, and then in using computers to analyze them in order to determine the presence of defects in the containers.

In order to detect defects in containers, it is known in the state of the art, e.g. as described in patent application EP 1 560 018, to prepare a digital mask and to compare the images taken with the digital mask. In the specific situation of that patent, the containers are set into rotation about their axes of symmetry and a series of images is taken. In that system of inspection with rotation, a drawback of using digital masks appears when it is necessary to manage a plurality of different digital masks in order to take account of particular features such as patterns on the containers, since while the images are being taken, those features will appear in different positions as the article rotates about its axis.

In accordance with that document, it should be considered that a digital mask is an image, i.e. an array of values or pixels, that is suitable for superposing on the image for treatment, with the values of its pixels modifying the way in which the pixels in the image for treatment are treated. For example, the values of the pixels in the digital mask are used as a map of local thresholds with which the pixels of the image for treatment are compared. Nevertheless, the values of the digital masks may also define a filter size, a gain, etc., for application to each of the pixels in the image for treatment.

It is also known from the article published in "Glass worldwide", Issue 33, 2011, page 32 "Quality control solutions for cosmetics" to provide a method of analyzing images of containers in which a digital mask is constructed by training on the basis of actual production, which training makes it possible to take account of various effects that occur recurrently in bottles, such as for example shadows at the edges of the articles.

Because the containers carrying patterns are randomly oriented at the moment the images are taken, that technique cannot be applied to a zone in which a pattern might be present, since training would lead to detection sensitivity being completely eliminated detection sensitivity in that region.

It is known to locate certain types of pattern in the images of containers and to apply image treatment away from those patterns, in order to avoid considering said patterns as defects. However, under such circumstances, the patterns themselves are not analyzed, even if they do indeed contain defects. That amounts to locating "no treatment" zones over the patterns.

When said patterns are etched in the glass, as applied when inspecting glass containers immediately after they have been fabricated, they also suffer from rather large variability in contrast that means that they cannot be considered merely as simple binary geometrical shapes.

It is thus particularly difficult to detect defects in containers that present visible patterns such as crests or identification or positioning marks, for example. The treatment of the images needs to take account of the presence of such visible patterns in the images that are taken. A major difficulty also appears in detecting a defect that is located in a visible pattern of the container.

In the state of the art, an optical method is also known from patent application WO 97/06429 that serves to detect defects in container threads, which method seeks to take a multitude of images of the containers and to find determined treatment zones for detecting defects. For each treatment zone, all of the pixels in the zone are compared with a threshold value. The threshold value is calculated solely on the basis of an overall statistic for each zone. That technique does not make it possible to perform fine analysis of complex images and to detect defects in containers that present visible patterns such as crests or identification or positioning marks, for example.

Document US 2005/259868 describes an optical method of inspecting objects that consists in making a series of images of the object and in comparing at least one image of the acquired series with an image taken in a prerecorded series of images. That document teaches subjecting images to a geometrical operation comprising a shift in translation and/or a movement in rotation prior to comparing images with one another. Such a method is not suitable for inspecting patterns in relief carried by transparent objects, when the patterns are variable and when their images also vary enormously as a function of the position of the object relative to the lighting and observation devices, because refraction does not take place in the type of object observed using that method.

The present invention seeks to remedy the drawbacks of the prior art by proposing a novel optical method for inspecting transparent or translucent containers having visible patterns, the method being designed in particular to detect defects in zones of the containers that include such visible patterns, it being possible for the inspection to be performed successfully regardless of the positions of the visible patterns in the images taken.

To achieve such an object, the optical method of the invention seeks to use a vision system for inspecting containers made of transparent or translucent material and including at least one visible pattern.

According to the invention, the method consists:
  in illuminating the containers traveling past the vision system;

in forming at least one image of each container traveling past the vision system, each image possessing a determined number of pixels, each pixel having a respective intensity level;

in determining, in the image of the container, at least one treatment zone including at least one visible pattern for inspection, and at least one search zone in which there appears at least one marker visible pattern;

in preparing a digital mask at least for the treatment zone of the images;

in determining the position and the orientation of the marker visible pattern in said search zone of the image of the container;

in applying a geometrical transformation to the digital mask or to the treatment zone, which transformation is a function of the position and the orientation of the marker visible pattern, so as to be capable during a treatment step of placing the mask and the treatment zone into a position in which they coincide;

in applying image treatment to each pixel of the treatment zone, the treatment depending on the intensity value of the coincident pixel of the digital mask, in order to detect the presence of any defect in the container; and updating the digital mask by:
  taking account of at least one image of the containers; and
  deciding whether or not to modify the digital mask as a function of said image, the modification of the mask consisting:
    in determining the position and the orientation of the visible pattern for inspection in the treatment zone of the images;
    in applying a geometrical transformation to the treatment zone of the image or to the mask so as to be capable of placing the mask and the treatment zone in a position in which they coincide; and
    in melding at least the treatment zone of the image and of the mask in order to update the digital mask.

Furthermore, the method of the invention may also present in combination at least one and/or another of the following additional characteristics:

preparing the digital mask in an initialization step, from at least one image of a container;

applying image treatment to each pixel of the treatment zone, in which treatment each pixel of the treatment zone is compared with the coincident pixel of the digital mask;

analyzing the image in order to detect defects in the visible pattern;

applying a shift in translation and/or a rotation and/or an anamorphosis as the geometrical transformation; and prior to the treatment step, performing a filtering step on the images taken of the containers, and taking account of the images to which said filtering step has been applied in the step of updating the mask.

Various other characteristics appear from the following description made with reference to the accompanying drawings which show implementations of the invention as non-limiting examples.

FIG. 1 is a diagrammatic view of a vision system adapted in particular to inspect container bottoms, each including at least one visible pattern.

FIG. 1A shows an example of an image of a container bottom in which there can be seen a visible pattern.

FIG. 2 is a diagrammatic view of a vision system adapted in particular to inspect a container wall provided with at least one visible pattern.

Figure 2A:
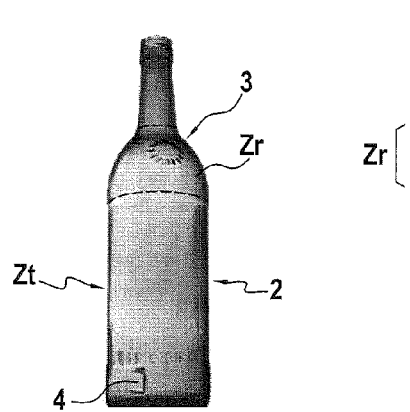
FIG. 2A shows an example of an image of a container having a visible pattern on its wall.

As can be seen in FIGS. 1 and 2, the invention relates to using a vision system 1 to inspect containers 2 made of transparent or translucent material, such as bottles, jars, or flasks made of glass and provided with at least one visible pattern 3 such as decoration, a crest, a positioning lug or notch, and/or an identification or authentication mark such as a mold number. Such a visible pattern may be obtained in particular by molding, by etching, or by printing.

The invention seeks to inspect containers in order to detect defects situated in particular in the zones of containers in which at least one visible pattern 3 is present. The inspection method seeks more particularly to inspect containers for which repetitive handling is not guaranteed, i.e. for which the positions and orientations of the containers 2 relative to the vision system 1 might vary from one container to another. In general, the containers 2 are bodies of revolution about a vertical axis, and they are presented to an inspection station at random orientations about their axis of symmetry.

In conventional manner, the vision system 1 is adapted to take one or more images of each container 2 traveling in succession at a high rate past the vision system. Naturally, the vision system 1 is adapted or configured to take images of the containers 2, each image having at least one treatment zone Zt defined therein in which there appears at least one selected visible pattern 3, also referred to as the visible pattern for inspection. The treatment zone Zt corresponds to the zone of the container that is inspected in order to determine whether or not the container is in compliance. This treatment zone Zt that includes at least one selected visible pattern 3 may be limited to the region covered by that visible pattern 3 or it may cover an area that is greater than the area occupied by the visible pattern 3. The purpose of defining a treatment zone is to enable inspection to be performed within the visible pattern 3 and/or in the proximity of said visible pattern.

FIGS. 1 and 1A show an implementation in which the vision system 1 is adapted to inspect the bottoms $2_1$ of containers 2, each of which includes at least one visible pattern 3. In this example, the vision system 1 has a light source 5 situated under the bottom $2_1$ of the container 2 and a camera 6 provided with a lens situated above the container 2. The camera 6 is connected to a unit 7 for acquiring and processing images I taken by the camera for each container 2. FIG. 1A shows an example of an image I of the bottom of a container for inspection in which there is defined at least one treatment zone Zt including at least one selected visible pattern 3 for inspection, namely a manufacturer's trademark or an indication of content.

Figure 2B:
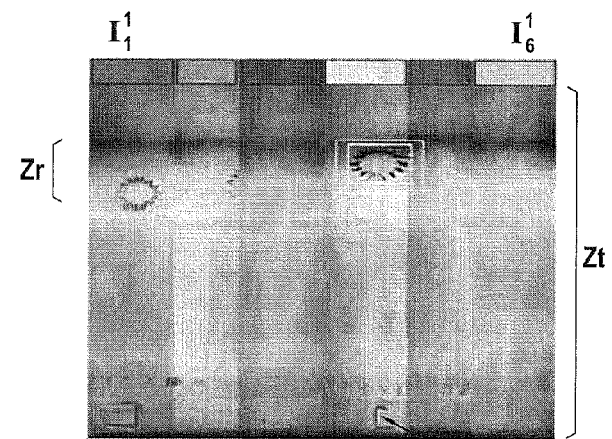
FIG. 2B shows a series of concatenated anamorphic images and shots of the container shown in FIG. 2A traveling past the vision system.

FIGS. 2A to 2B show another implementation in which the vision system 1 is adapted to inspect the walls $2_2$ of containers 2. In this example, the treatment zone Zt relates to a portion of the wall in which there appears a crest as the visible pattern 3 for inspection. In this example, the vision system 1 includes at least one light source (not shown) and a series of cameras 6 each having its own lens (there being six of them in the example shown), which cameras are distributed angularly so that the images taken by the various cameras 6 cover the entire periphery of each container 2 traveling past the vision station 1. Advantageously, the cameras 6 are arranged in such a manner that the images taken by two adjacent cameras cover a common zone of the container so as to be sure of being able to inspect the entire circumference of the container 2. FIG. 2B shows an example of six thumbnail images $I^1_1, I^1_2, I^1_3, \ldots, I^1_6$ for the same container, some of which thumbnails include the visible pattern 3 for inspection, namely the crest.

Naturally, the vision system 1 may be made in any appropriate manner, other than as described in the example. Regardless of the way with which is it made, the vision system 1 is capable, for each container 2 traveling in succession past the vision system, of illuminating the container and of taking at least one image $I_i$ of the container. Each image $I_i$ taken possesses a determined number of pixels, each having a given level of intensity.

The inspection method of the invention thus consists in selecting at least one treatment zone Zt including at least one visible pattern 3 for inspection, over a series of containers 2 caused to travel in succession past the vision station 1.

Figure 3:
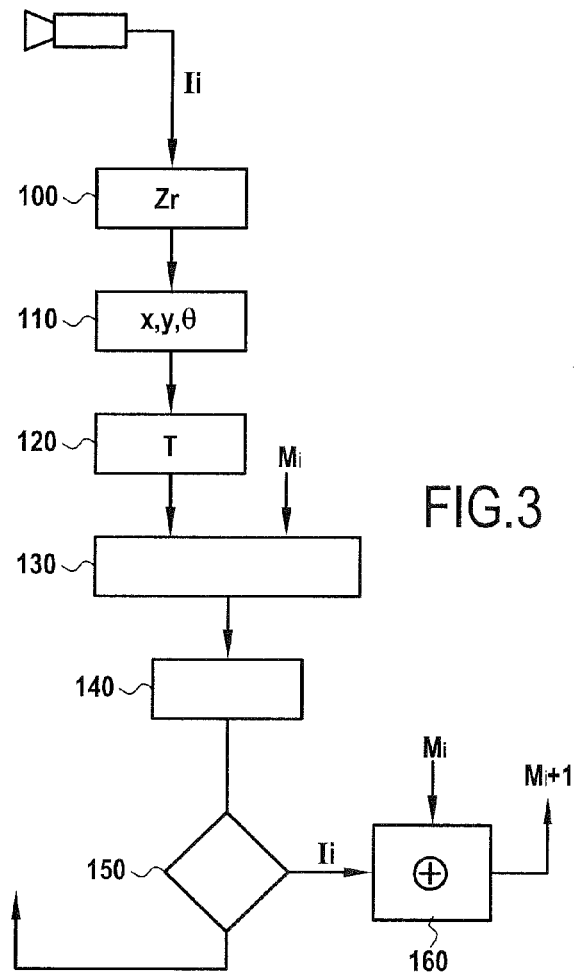
FIG. 3 is a simplified flow chart of the method in accordance with the invention.

Additionally, and as shown in FIG. 3, the method of the invention consists in a step 100 of selecting a "marker" visible pattern 3 and in considering at least one search zone Zr in the images taken $I_i$, the search zone Zr having at least one "marker" selected visible pattern appearing therein. It should be observed that the marker visible pattern 3 situated in the search zone Zr may optionally correspond to the visible pattern 3 for inspection present in the treatment zone Zt. In the example shown in FIG. 2A, the search zone Zr corresponds to a zone of limited height in the images, corresponding substantially to the shoulders of the containers, and in which there is situated as a visible pattern 3 the crest that also forms a part of the treatment zone Zt. Naturally, as mentioned above, the marker visible pattern 3 that is situated in the search zone Zr need not correspond to the visible pattern 3 for inspection that is present in the treatment zone Zt. Thus, by way of example, provision may be made for the treatment zone to include the crest as the visible pattern for inspection while the search zone includes a positioning notch 4 as its marker visible pattern 3. In a preferred implementation, the search zone Zr and the treatment zone Zt have a visible pattern 3 in common, i.e. the visible pattern for inspection corresponds to the marker visible pattern.

The method of the invention consists in a step 110 of locating the selected visible pattern 3 (or marker) in the search zone Zr. In other words, this locating step consists in determining the position and the orientation of the marker visible pattern 3 in the image $I_i$. It should be understood that this step makes it possible, in a given frame of reference, to determine the coordinates x, y and the orientation θ of the visible patterns 3 that appear in the various images $I_i$ of the containers 2. The positions of the visible patterns 3 in the images $I_i$ can vary insofar as the containers 2 occupy different positions and/or orientations as they are taken to the vision system 1, and in particular while the images are being taken.

More precisely, during a training stage this locating step consists in recording morphological and/or textural and/or photometric characteristics of the selected visible pattern 3 (or marker). In order to locate the selected visible pattern (or marker), the method consists in using any conventional search method (e.g. using pattern matching) to search for such characteristics present in the search zone Zr.

This locating step 110 serves to enable a digital mask Mi to be properly applied to the images $I_i$ that have been taken during a treatment step 130. Thus, the method of the invention consists in using a digital mask Mi for at least one treatment zone Zt in the images that includes at least the visible pattern 3 for inspection. The treatment zone Zt corresponds to the search zone Zr or to a portion only of the search zone Zr or covers the search zone completely and also extends outside the search zone. The visible mask Mi thus comprises a determined number of pixels, each having a determined intensity level (or gray level) within this treatment zone Zt. Preparation of the digital mask Mi is described in greater detail below.

The method of the invention then consists in a step 120 in applying a geometrical transformation T so that during the treatment step 130, the digital mask Mi and the treatment zone Zt of the images are arranged to coincide. It should be understood that the geometrical transformation T that is applied results from or depends on the result of locating the visible pattern 3 (or marker) as performed during step 110.

In the example shown in FIG. 3, the geometrical transformation T is applied to the images $I_i$. It is possible to envisage an implementation in which the geometrical transformation T is applied to the digital mask Mi instead of to the images $I_i$. This step of digital transformation T enables the pixels of the digital mask Mi to be caused to coincide with or be superposed on the pixels of the treatment zone Zt of the images $I_i$. Thus, in general terms, the pixels $\underline{m}$ of the digital mask Mi and the pixels $\overline{p}$ of the treatment zone Zt are placed in a common X, Y reference frame such that the coordinates of the pixels can be written respectively m(x,y) for the digital mask Mi and p(x,y) for the treatment zone Zt. Examples of this geometrical transformation T are given in the description below.

The method of the invention then consists, in the treatment step 130, in applying image treatment to each pixel of the treatment zone Zt in the images $I_i$, which treatment depends on the intensity value of the coincident pixel of the digital mask Mi. It should be considered that the image treatment is performed for each pixel p(x,y) in the treatment zone Zt of the image, taking account of the corresponding or coincident pixel m(x,y) of the digital mask Mi.

The image treatment may comprise at least a step of comparing the pixels p(x,y) of the image with the pixels m(x,y) of the digital mask Mi, or indeed performing the following treatment operations:

$$p(x,y)-m(x,y)$$

$$p(x,y)/m(x,y)$$

$$a*p(x,y)+b*m(x,y),$$

where a and b are coefficients.

The method of the invention then consists, in a step 140, in analyzing the results of the treatment step in order to determine whether the container presents a defect, in particular in the treatment zone Zt.

The method of the invention then consists, in a step 150, in determining whether or not to update the digital mask Mi. In a step 160, the method of the invention consists in updating the digital mask Mi as a function of the intensity levels of the pixels in the treatment zone Zt. This updating step 160 makes it possible, e.g. using statistical or mathematical rules to cause the digital mask Mi to evolve to a greater or lesser extent.

The choice (step 150) of whether or not to modify the digital mask Mi may depend on various factors, such as the image under consideration, the current state of container production, e.g. as determined by statistical analysis, and/or more or less severe quality control requirements. In a simplified first variant of the invention, for each inspected container, all of the images contribute continuously to the evolution of the digital mask. In another variant implementation, the digital mask Mi is caused to evolve only during a limited period corresponding to the beginning of container production. In another variant implementation, the digital mask Mi is updated by taking account only of images of containers that are seen to be without any defects. In this particular implementation, the digital mask Mi is modified to become Mi+1 when the analysis step determines that the container 2 does not have any defect. Under such circumstances, the digital mask Mi is modified so as to incorporate pixel by pixel at least a portion of the intensity values of the pixels in the treatment zone Zt. The advantage of making the digital mask by melding a large number (several tens) of images and thus of containers, is that it makes it possible automatically to obtain a mean image of the containers, which mean image may be considered as being an image of containers without defects, thereby automatically creating detection sensitivity that is locally variable.

The method of the invention consists in renewing the above-described treatment steps for the next container 2, with a digital mask Mi+1 that might possibly be modified.

The method of the invention thus installs a principle of detecting defects that relies on a running accumulation of pre-treated images that are compared with the image of the container under inspection. This detection principle serves to eliminate information that occurs repeatedly (shadows or patterns), and thus to obtain better measurement sensitivity in treatment zones that are disturbed by the presence of visible patterns, and possibly even to use the same detection criteria for the entire treatment zone, including for differing visible patterns.

The method of the invention thus consists in preparing a digital mask Mi:
  by taking account of at least one image of the container 2;
  by determining the position and the orientation of the visible pattern 3 (or marker) in the search zone Zr of at least said image;
  by applying a geometrical transformation that is a function of the position and the orientation of the marker visible pattern 3, either to the treatment zone Zt of said image or to the mask, so as to place the treatment zone Zt and the digital mask in a position where they coincide; and
  by melding at least the treatment zone of the image and the digital mask in order to update the digital mask Mi.

It can be seen from the above that the digital mask Mi is made by melding image treatment zones Zt. In general, melding an image with the digital mask consists in modifying the values of coinciding pixels in the digital mask. This modification may be performed in various ways, such as, by way of example: systematic or conditional linear combination of the values of a pixel in the digital mask and of a pixel in the image, with or without a threshold, while taking account of neighboring pixels or a neighboring group of pixels.

In a variant implementation, the method consists in preparing the digital mask in an initialization step, starting from at least one image of a container that, by way of example, does not include any defects.

It can be seen from the above description, that the random orientations and positioning of the containers 2 are corrected so as to cause the pixels of the images to coincide strictly with the pixels of the digital mask. This geometrical transformation may be performed in various ways.

When the images $I_i$ are taken of the bottom $2_1$ of the container 2 (FIGS. 1 and 1A), the images may be righted by performing a geometrical transformation on the image on the basis of determining the angle of rotation and the shift of the visible pattern 3 relative to an origin position or a fixed reference.

When the images $I_i$ are taken of the walls of the container by a series of cameras 6 (FIGS. 2, 2A, 2B), the geometrical transformation on the images makes use of at least one anamorphosis treatment. Given that the container 2 is in the form of a body of revolution, each camera 6 applies anamorphosis treatment so that all of the shots taken possess a common frame of reference for treatment. The anamorphosis calculations serve to obtain a plane representation of the wall of the container which itself is generally cylindrical. The method enables the shots or thumbnails obtained after anamorphosis to be concatenated so as to provide a rolled-out representation of the entire wall of the container (FIG. 2B). Thereafter, it is possible to locate the visible pattern 3 in one of the concatenation of thumbnail images that have been subjected to anamorphosis.

According to an advantage characteristic of the invention, the method consists in forming a step of filtering the images taken of the containers prior to performing the treatment step. Thus, in order to improve the quality of the images taken, provision may be made to correct its histogram, to reduce noise by means of lowpass filters, or to reinforce, local contrast of defects in the image by using filters of the highpass type. Such filtering may be performed before or after the geometrical transformation step.

This filtering step is applied to the images taken into consideration when updating the digital mask.

The invention is not limited to the examples described and shown since various modifications may be applied thereto without going beyond its ambit. The invention also applies to analyzing infrared images obtained directly from the radiation emitted by hot bottles.

The invention claimed is:

1. An optical method of using a vision system (1) to inspect containers (2) made of transparent or translucent material and including at least one visible pattern (3), the method being characterized in that it consists:
  in illuminating the containers (2) traveling past the vision system (1);
  in forming at least one image ($I_i$) of each container (2) traveling past the vision system (1), each image possessing a determined number of pixels, each pixel having a respective intensity level;
  in determining, in the image of the container, at least one treatment zone (Zt) including at least one visible pattern for inspection, and at least one search zone (Zr) in which there appears at least one marker visible pattern (3);
  in preparing a digital mask (Mi) at least for the treatment zone (Zt) of the images;
  in determining the position and the orientation of the marker visible pattern (3) in said search zone (Zr) of the image of the container;
  in applying a geometrical transformation to the digital mask (Mi) or to the treatment zone (Zt), which transformation is a function of the position and the orientation of the marker visible pattern (3), so as to be capable during a treatment step of placing the mask (Mi) and the treatment zone (Zt) into a position in which they coincide;
  in applying image treatment to each pixel of the treatment zone (Zt), the treatment depending on the intensity value of the coincident pixel of the digital mask (Mi), in order to detect the presence of any defect in the container; and
  updating the digital mask (Mi) by:
    taking account of at least one image ($I_i$) of the containers (2); and
    deciding whether or not to modify the digital mask as a function of said image, the modification of the mask consisting:
      in determining the position and the orientation of the visible pattern (3) for inspection in the treatment zone (Zt) of the images;
      in applying a geometrical transformation to the treatment zone (Zt) of the image or to the mask so as to be capable of placing the mask (Mi) and the treatment zone (Zt) in a position in which they coincide; and in melding at least the treatment zone (Zt) of the image and of the mask in order to update the digital mask (Mi).

2. A method according to claim 1, characterized in that it consists in preparing the digital mask in an initialization step, from at least one image of a container.

3. A method according to claim 1, characterized in that it consists in applying image treatment to each pixel of the treatment zone (Zt), in which treatment each pixel of the treatment zone (Zt) is compared with the coincident pixel of the digital mask.

4. A method according to claim 1, characterized in that it consists in analyzing the image in order to detect defects in the visible pattern.

5. A method according to claim 1, characterized in that it consists in applying a shift in translation and/or a rotation as the geometrical transformation.

6. A method according to claim 1, characterized in that it consists in applying an anamorphosis as the geometrical transformation.

7. A method according to claim 1, characterized in that, prior to the treatment step, it consists in performing a filtering step on the images taken of the containers, and in taking account of the images to which said filtering step has been applied in the step of updating the mask.

* * * * *